US00PP27065P3

(12) United States Plant Patent
Zaiger et al.

(10) Patent No.: US PP27,065 P3
(45) Date of Patent: Aug. 16, 2016

(54) INTERSPECIFIC TREE NAMED 'AUTUMN FRITZ'

(50) Latin Name: **Interspecific *Prunus* species**
Varietal Denomination: Autumn Fritz

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 77 days.

(21) Appl. No.: 14/121,881

(22) Filed: Oct. 31, 2014

(65) Prior Publication Data

US 2016/0128249 P1 May 5, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

(56) References Cited

PUBLICATIONS

UPOV hit on 'Autumn Red' Nectarine, Jun. 15, 1976.*

* cited by examiner

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Fruit with an attractive red skin color.
3. Fruit with good flavor and eating quality.
4. Fruit maturing very late in the season.
5. Fruit with good storage and shipping quality.

1 Drawing Sheet

Botanical designation: Interspecific *Prunus* species.
Variety denomination: 'Autumn Fritz'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Fall Fiesta' Interspecific (U.S. Plant Pat. No. 22,428), 'Flavorfall' Interspecific (U.S. Plant Pat. No. 11,990), 'Candy Stripe' Interspecific (U.S. Plant Pat. No. 17,828) and our non-patented proprietary interspecific seedling selections with the field identification numbers '288LK54', '41EH357', '67Z80', '82EG355', '324LF168', '19HD447' and '31M208'.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; *Prunus salicina, Prunus armeniaca* and *Prunus persica*. It was originated by us in our experimental orchard located near Modesto, Calif. as a first generation cross between our proprietary non-patented interspecific seedling selections with the field identification numbers '19HD447' and '31M208'. The seed parent (19HD447) interspecific (non-patented) originated from a cross of our non-patented proprietary interspecific seedling '288LK54' and 'Candy Stripe' Interspecific (U.S. Plant Pat. No. 17,828). The non-patented interspecific pollen parent (31M208) originated as an open pollinated seedling selection from our proprietary non-patented interspecific seedling '41EH357' which is a first generation cross from our proprietary non-patented interspecific seedling '67Z80' and 'Flavorfall' Interspecific (U.S. Plant Pat. No. 11,990). A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2007 for additional asexual propagation and commercialization.

ASEXUAL REPRODUCTION OF THE VARIETY

In 2007 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree (Plum×Apricot×Peach) which has vigorous, upright growth and is a regular and productive bearer of large size, yellow flesh, clingstone fruit with good flavor and eating quality. The fruit is further characterized by is attractive red skin color, by holding firm on the tree 2 weeks after maturity (shipping ripe) and having good storage and shipping quality. In comparison to its non-patented interspecific seed parent (19HD447) the fruit of the new variety has firmer flesh and is approximately 19 days later in maturity. In comparison to its pollen parent (31M208) interspecific (non-patented) the fruit of the new variety is approximately 44 days later in maturity. In comparison to the commercial variety 'Fall Fiesta' Interspecific (U.S. Plant Pat. No. 22,428) the fruit of the new variety has red skin color compared to blue black and is approximately 31 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

- *Size*.—Large, usually pruned to 3 to 3.5 meters in height and width for economical harvesting of fruit. Varies with different cultural practices.
- *Vigor*.—Vigorous, tree growth of approximately 1.5 to 2 meters the first growing season. Varies with cultural practices, soil type, fertility and climatic conditions.
- *Form*.—Upright, usually pruned to vase shape.
- *Branching habit*.—Upright, crotch angle approximately 25°, increases with heavy crop load.
- *Productivity*.—Productive, thinning and spacing of fruit desirable for marketable size. Fruit set varies with climatic conditions during bloom time.
- *Bearer*.—Regular, adequate fruit set 5 consecutive years. No alternate bearing observed.
- *Fertility*.—Self-sterile, pollinator required.
- *Density*.—Medium dense, usually pruned to vase shape to increase amount of sunlight to center of tree to enhance fruit color, Brix and health of fruit spurs.
- *Hardiness*.—Hardy in all stone fruit growing areas of California. Tree grown in USDA Hardiness Zone 9. Winter chilling requirement approximately 1000 hours at or below 45° F.

Trunk:

- *Size*.—Large. Average circumference of 61.0 cm at 20.3 cm above ground on a 7 year old tree.
- *Stocky*.—Medium stocky.
- *Texture*.—Medium shaggy, becomes rougher with age.
- *Color*.—Varies from 2.5Y 5/2 to 10YR 2/2.

Branches:

- *Size*.—Medium. Average circumference 13.0 cm at 1.2 meters above ground. Crotch angle approximately 25°, increases with heavy crop load.
- *Surface texture*.—New growth relatively smooth. Mature growth medium rough, roughness increases with age.
- *Lenticels*.—Average number 47 in a 25.8 sq cm section. Average length 5.1 mm. Average width 1.7 mm. Color varies from 7.5YR 4/8 to 10YR 5/8.
- *Color*.—New growth varies from 5GY 5/6 to 5GY 5/8. Mature growth varies from 10YR 3/2 to 10YR 2/2, varies with age of growth.

Leaves:

- *Size*.—Medium. Average length 90.0 mm. Average width 42.0 mm.
- *Form*.—Oblanceolate.
- *Apex*.—Acuminate.
- *Base*.—Cuneate.
- *Margin*.—Doubly serrate.
- *Thickness*.—Medium.
- *Surface texture*.—Upper surface relatively smooth, slight indentations over midrib and leaf veins. Lower surface relatively smooth, except for small ridges created by midrib and pinnate venation. Both upper and lower surfaces glabrous.
- *Petiole*.—Medium. Average length 12.5 mm. Average width 1.2 mm. Longitudinally grooved. Surface — pubescent. Color varies from 10Y 6/4 to 10Y 7/4.
- *Glands*.—Type — globose. Size — small to medium. Average length 0.9 mm. Average diameter 0.7 mm. Average number 3, varies from 2 to 4. Located primarily on the base of leaf blade and upper portion of the petiole. Color varies from 2.5YR 3/4 to 2.5GY 6/8.
- *Stipules*.—None present.
- *Color*.—Upper surface varies from 5GY 4/4 to 2.5GY 5/4. Lower surface varies from 5GY 5/4 to 5GY 6/4. Midvein color varies from 5GY 8/2 to 10Y 8/2.

Flower buds:

- *Size*.—Small to medium. Average length 9.4 mm. Average diameter 5.1 mm.
- *Hardiness*.—Hardy with respect to California winters.
- *Form*.—Conical, becoming elongated just before opening.
- *Pedicel*.—Average length 7.1 mm. Average width 0.7 mm. Color varies from 2.5GY 6/6 to 2.5GY 6/8. Surface — glabrous.
- *Color*.—N 9.5/(white).
- *Number of buds per spur*.—Average 8, varies from 7 to 9. Varies with age of spur.

Flowers:

- *Blooming period*.—Date of First Bloom Mar. 7, 2013. Date of Petal Fall Mar. 17, 2013, varies slightly with climatic conditions.

*Size*.—Small to medium. Average height 9.8 mm. Average diameter 16.4 mm.

*Petals*.—Normally 5, alternately arranged to sepals. Size — small to medium. Average length 8.7 mm. Average width 6.2 mm. Form — elliptical. Arrangement — free. Petal apex — rounded. Petal base — rounded to somewhat truncated. Margin — sinuate. Color N 9.5/(white). Both upper and lower surfaces glabrous.

*Sepals*.—Normally 5, alternately arranged to petals. Size — small. Average length 2.7 mm. Average width 2.4 mm. Shape — triangular. Apex rounded to triangular. Margin — finely serrated. Both upper and lower surfaces glabrous. Color — upper surface varies from 5GY 6/6 to 5GY 5/6. Lower surface varies from 5GY 6/6 to 5GY 5/6.

*Stamens*.—Average number per flower 33. On average, the stamens are equal to slightly above the height of the petals. Average filament length 7.7 mm. Filament color N 9.5/(white). Anther color varies from 5Y 8/10 to 5Y 7/10.

*Pollen*.—Self-sterile, pollinator required. Color varies from 2.5Y 7/12 to 5Y 7/10.

*Pistil*.—Number — normally 1. Average length 8.3 mm. Position of stigma an average of 1.4 mm below anthers. Surface — glabrous. Color varies from 10Y 8/6 to 2.5GY 8/6.

*Fragrance*.—Heavy aroma.

*Color*.—N 9.5/(white).

*Pedicel*.—Average length 8.0 mm. Average width 0.9 mm. Color varies from 2.5GY 6/8 to 2.5GY 5/8. Surface — glabrous.

*Number flowers per flower bud*.—Average 3, varies from 2 to 4.

Fruit:

*Maturity when described*.—Firm ripe and ready for consumption.

*Date of first picking*.—Oct. 20, 2013.

*Date of last picking*.—Oct. 28, 2013, varies slightly with climatic conditions.

*Size*.—Medium to large. Average diameter axially 58.7 mm. Average transversely in suture plane 55.7 mm. Average weight 159.0 grams, varies slightly with fertility of the soil, amount of thinning and climatic conditions.

*Form*.—Globose.

*Suture*.—Nearly smooth, extends from base to apex.

*Ventral surface*.—Slightly lipped.

*Apex*.—Rounded.

*Base*.—Varies from flat to rounded.

*Stem cavity*.—Rounded to slightly elongated in suture plane. Average depth 4.1 mm. Average diameter 3.3 mm.

Stem:

*Size*.—Medium. Average length 13.4 mm. Average diameter 2.0 mm.

*Color*.—Varies from 5Y 6/6 to 5YR 4/6.

Skin:

*Thickness*.—Medium.

*Surface*.—Smooth to very slightly waffled.

*Bloom*.—Moderate amount, completely covered.

*Tendency to crack*.—Very slight.

*Color*.—Ground color varies from 10YR 6/8 to 10YR 7/10. Overspread with 7.5R 3/8 to 7.5R 3/10.

*Tenacity*.—Tenacious to flesh.

*Astringency*.—Undetected.

Flesh:

*Ripens*.—Evenly.

*Texture*.—Firm, meaty, crisp.

*Fibers*.—Few, small, tender.

*Firmness*.—Firm, having good handling and shipping quality.

*Aroma*.—Slight.

*Amydgalin*.—Undetected.

*Eating quality*.—Good.

*Flavor*.—Good, having a good balance between acid and sugar.

*Juice*.—Moderate amount, enhances flavor.

*Acidity*.—Not available.

*Brix*.—Average Brix 19.0°, varies slightly with amount of fruit per tree and climatic conditions.

*Color*.—Varies from 2.5Y 7/6 to 10R 3/10.

*Pit cavity*.—Average length 25.0 mm. Average width 16.9 mm. Average depth 5.4 mm. Color varies from 2.5YR 4/10 to 10R 4/10.

Stone:

*Type*.—Clingstone, medium adherence.

*Size*.—Medium. Average length 24.2 mm. Average width 15.9 mm. Average thickness 9.4 mm.

*Form*.—Ovoid.

*Base*.—Flat.

*Apex*.—Pointed. Average length 2.7 mm.

*Surface*.—Slightly pitted throughout. One shallow groove on each side of suture extending from base to apex.

*Sides*.—Unequal, one side extending further outward from suture plane.

*Ridges*.—Small, extending from base toward apex.

*Tendency to split*.—None.

*Color*.—Varies from 7.5YR 5/6 to 7.5YR 4/4 when dry.

Kernel:

*Size*.—Small to medium. Average length 13.6 mm. Average width 9.3 mm. Average depth 5.6 mm.

*Form*.—Ovoid.

*Viability*.—Viable, complete embryo development.

*Skin color*.—Varies from 10YR 5/8 to 10YR 4/8.

Use:

*Dessert*.—Market — local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

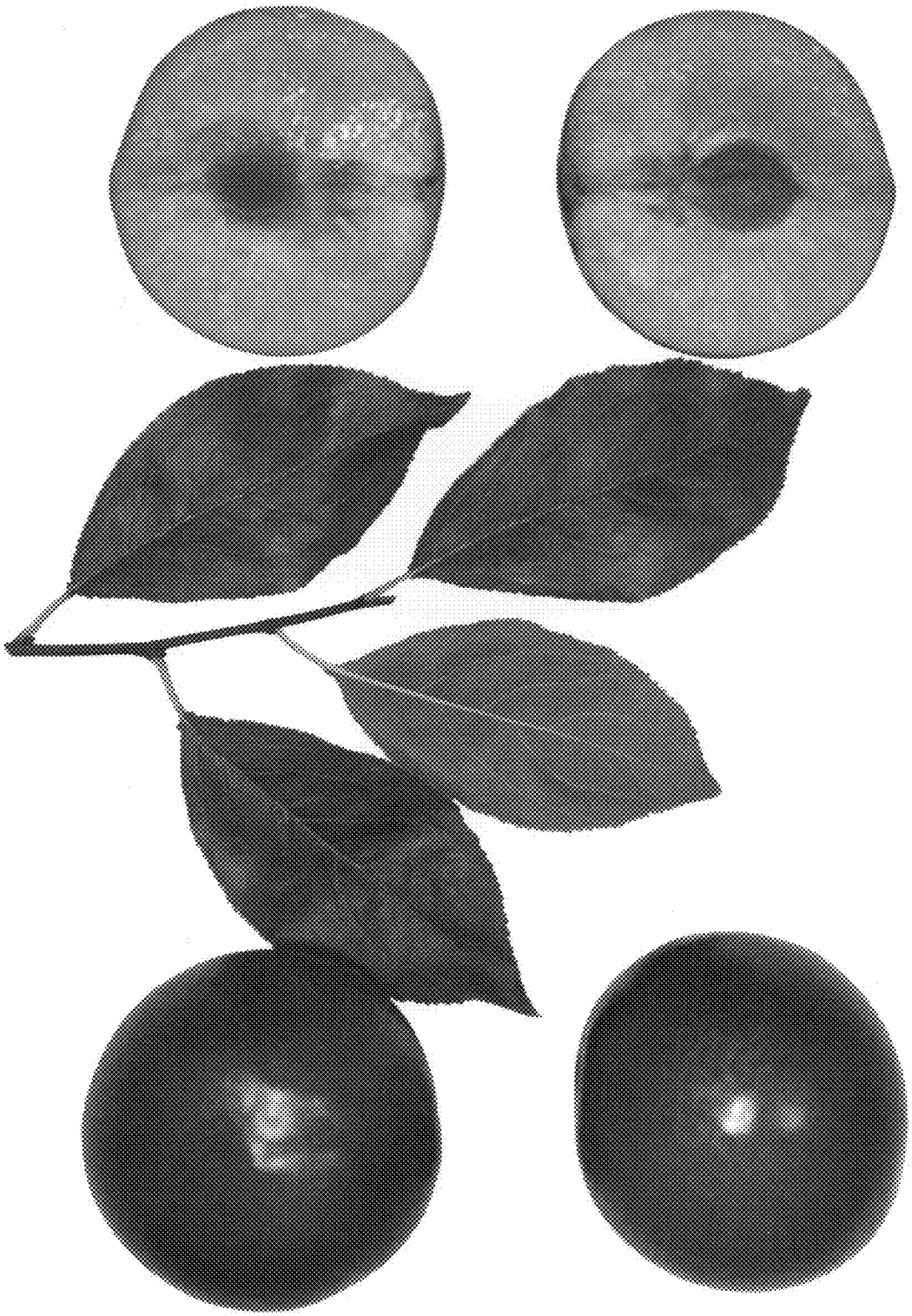

* * * * *